(12) United States Patent
Iordache et al.

(10) Patent No.: US 8,913,715 B2
(45) Date of Patent: Dec. 16, 2014

(54) MEDICAL IMAGING SYSTEM AND METHOD

(75) Inventors: Razvan Gabriel Iordache, Paris (FR); Remy Andre Klausz, Neuilly sur Seine (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/968,951

(22) Filed: Dec. 15, 2010

(65) Prior Publication Data

US 2011/0150172 A1  Jun. 23, 2011

(30) Foreign Application Priority Data

Dec. 22, 2009  (FR) ...................................... 09 59360

(51) Int. Cl.
| | |
|---|---|
| *A61B 6/03* | (2006.01) |
| *A61B 6/02* | (2006.01) |
| *A61B 6/00* | (2006.01) |
| *G06T 11/00* | (2006.01) |
| *G06T 11/20* | (2006.01) |

(52) U.S. Cl.
CPC . *A61B 6/025* (2013.01); *A61B 6/03* (2013.01); *A61B 6/502* (2013.01); *G06T 11/005* (2013.01); *G06T 11/206* (2013.01); *A61B 6/548* (2013.01); *G06T 2211/436* (2013.01)
USPC .......................................................... 378/25

(58) Field of Classification Search
CPC .. A61B 6/025; A61B 6/461; G06T 2211/436; G06T 2211/432
USPC .......................................... 378/21–27, 98.12
See application file for complete search history.

(56) References Cited

U.S. PATENT DOCUMENTS

| | | | |
|---|---|---|---|
| 6,196,715 B1 * | 3/2001 | Nambu et al. .................. | 378/197 |
| 6,447,164 B1 * | 9/2002 | Polkus .......................... | 378/206 |
| 2003/0118146 A1 | 6/2003 | Shida et al. | |
| 2005/0111616 A1 * | 5/2005 | Li et al. ........................... | 378/22 |
| 2007/0201610 A1 * | 8/2007 | Adachi et al. ..................... | 378/4 |
| 2007/0242868 A1 | 10/2007 | Stanton et al. | |
| 2009/0097615 A1 * | 4/2009 | Fischer et al. ............... | 378/98.3 |
| 2009/0268865 A1 * | 10/2009 | Ren et al. ......................... | 378/37 |

FOREIGN PATENT DOCUMENTS

| | | |
|---|---|---|
| FR | 2902218 A1 | 12/2007 |
| WO | 2007037937 A1 | 4/2007 |

OTHER PUBLICATIONS

Godfrey et al., Optimization of matrix inversion tomosynthesis (MITS) impulse response and modulation transfer function characteristics for chest imaging, 2006, Medical Physics, vol. 33, No. 3, pp. 655-667.*

Li et al., 3-d View Weighted Cone-beam Filtered Backprojection Reconstruction for Digital Tomosynthesis, 2007, SPIE, vol. 6510, pp. 4X-1 through 4X-8.*

Search Report and Written Opinion, Dated Jun. 29, 2010.

* cited by examiner

*Primary Examiner* — Toan Ton
*Assistant Examiner* — John Corbett
(74) *Attorney, Agent, or Firm* — GE Global Patent Operation; Marc A. Vivenzio

(57) ABSTRACT

A medical imaging device capable of determining the number of projections in which at least one point located above or at the level of the object support surface is present.

10 Claims, 3 Drawing Sheets

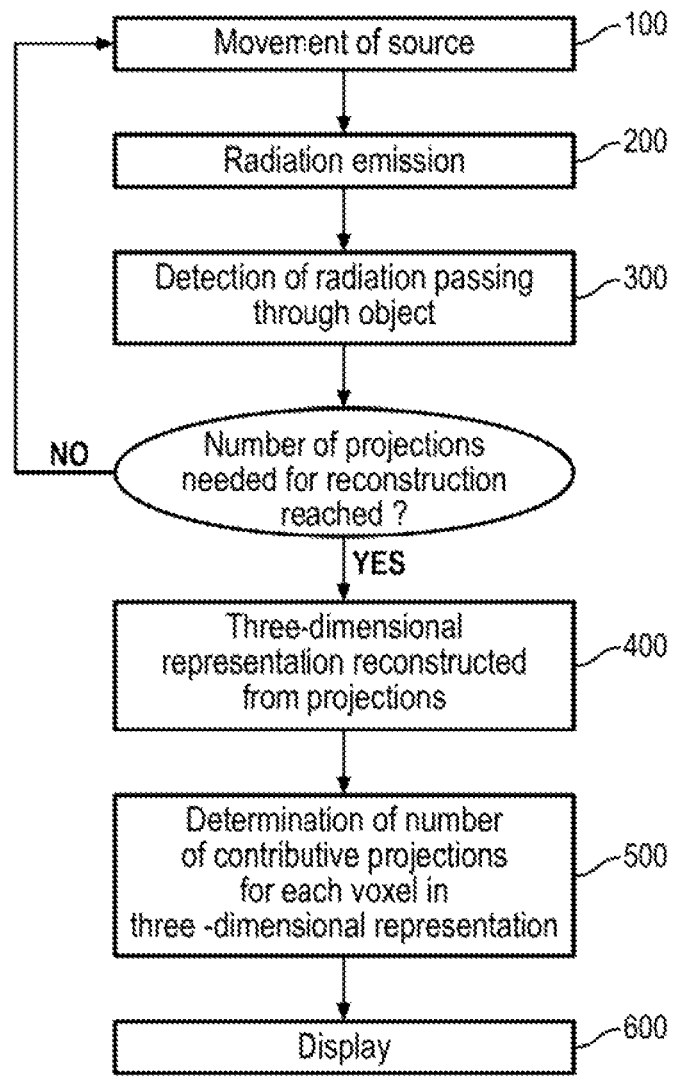

MEDICAL IMAGING SYSTEM AND METHOD

BACKGROUND OF THE INVENTION

1. Field of the Invention

The field of the invention concerns the area of medical imaging, particularly mammography.

2. Description of Related Art

Tomosynthesis is a variant of conventional planar tomography in which a limited number of radiographic projections of a patient's body organ is acquired in digital form at different angles relative to the patient. All the projections acquired from the different angles are then processed to obtain three-dimensional data on said patient organ. These three-dimensional data can be displayed as a set of sectional planes or in any other three-dimensional form.

Currently known tomosynthesis devices for mammography comprise an arm 15 carrying a radiation source 14 capable of emitting radiation, a radiation detector 17 capable of receiving the radiation, a planar support surface 26 for the object placed between the source 14 and the detector 17, a plate 74 placed between the object support surface 26 and the source 14 to compress the object 16 to be imaged, and processing means 32. The arm 15 carrying the source 14 can be moved about a first axis 19 in a plurality of positions 7. This arm 15 acts as positioner. The source is pivot-mounted on the arm to so that it can be oriented with respect to the object support surface. These movements of the source and arm about their respective rotation axes allow the radiographic projections of the breast 16 of the patient to be acquired at different angles during a sequence of radiation exposures.

The breast 16 is placed on the object support surface 26 so that the detector 17 can receive radiation which has passed through the inner structures of the breast 16. The detector 17 produces a signal which is processed by the processing means 32 to produce a radiographic projection of the inner structures of the breast 16. The arm 15 is then moved to a new position 7 to produce a radiographic view at a different angle, and so on. Using reconstruction techniques, all the radiographic projections are able to produce three-dimensional data of the breast 16.

One limitation specific to the above-described method is that the information used to reconstruct three-dimensional data may be incomplete outside a volume determined by the acquisition geometry. Existing systems do not provide any information to the user indicating beforehand whether the entirety of the structures of interest of the object can be reconstructed with nominal quality.

The purpose of the invention is therefore to propose a device and method to assist the user in the identification of anomalies in the imaged region, by providing information on the zone for which three-dimensional data of nominal quality will be obtained.

BRIEF DESCRIPTION OF THE INVENTION

For this purpose, a medical imaging device is provided that comprises an object support surface, a radiation source to emit radiation, a radiation detector capable of detecting the radiation emitted by the source. The radiation source can be moved in a plurality of positions about the object support surface. The radiation source emits radiation which is received by the detector at each position so as to obtain a plurality of projections corresponding to the plurality of positions of the radiation source, the device comprising processing means, for each point in a plane lying above or at the level of the object support surface, capable of determining the effective number of projections contributing towards reconstruction of three-dimensional data in the vicinity of this point, and thereby inferring incidence on the quality of the reconstructed three-dimensional data, and viewing means capable of presenting the user with information on the zone in which the quality of reconstructed three-dimensional data does not show any degradation subsequent to use of an effective number of projections that is lower than a predetermined acceptable threshold.

Preferred, but non-limiting, aspects of a method of the invention include a viewing means which may comprise display means capable of displaying a three-dimensional view reconstructed from the plurality of projections, said display means possibly being capable of presenting the user with information on the zone in which the quality of reconstructed three-dimensional information does not show any degradation resulting from use of an effective number of projections which is lower than a predetermined acceptable threshold.

The display means may further be capable of superimposing a different marker for each region of the three-dimensional representation in relation to the effective number of projections used to reconstruct said region. The display means may be capable of masking the regions whose quality is deteriorated resulting from use of an effective number of projections that is lower than the predetermined acceptable threshold.

The display means may be capable of giving a different display of the regions reconstructed from an effective number of projections that is higher than the predetermined acceptable threshold, and may also be capable of giving the regions reconstructed from an effective number of projections that is lower than the predetermined acceptable threshold.

The viewing means may comprise identification means which, prior to the acquisition of the plurality of projections, may locate points of the volume lying between the source and the plane of the object support surface in which the reconstructed three-dimensional data does not show any degradation resulting from use of an effective number of projections that is lower than the acceptable threshold; the identification means may be comprised of an illuminating device of said volume. The identification means may further comprise at least one video camera displaying an image of the object on which identification marks are superimposed designating the intersection of said volume with a reference plane.

The viewing means may comprise an illumination device to illuminate the surfaces of the object support surface limiting said volume. The identification means consist of at least one video camera displaying an image of the object on which identification marks are superimposed designating the intersection of said volume with a reference plane.

Embodiments of the invention also concern a medical imaging method that comprises moving a radiation source over a plurality of positions around an object support surface. Emission by the radiation source may occur at each position to irradiate an object arranged on the object support surface. For each position of the source, a radiation detector may detect the radiation, which has passed through the object, so as to obtain a plurality of radiographic projections. Reconstruction of a three-dimensional view from said radiographic projections may occur. The medical imaging method may determine, for each point in a plane lying above or at the level of the object support surface, the number of projections contributing towards reconstruction of the three-dimensional data in the vicinity of this point, and may thereby infer the incidence on the quality of the reconstructed three-dimensional data. The user may be presented with information on the zone in which the quality of reconstructed three-dimensional data does not show any degradation resulting from use of an effective number of projections that is less than a predetermined acceptable threshold.

Embodiments of the invention also concern a computer program product that comprises program code instructions to carry out the steps of the above-described method when said program is run on a computer.

BRIEF DESCRIPTION OF THE DRAWINGS

Other characteristics and advantages of embodiments of the system and method of the invention will become apparent form the following description which is solely illustrative and in no way limiting, to be read with reference to the appended drawings.

FIG. 4 is a schematic illustration of one embodiment of the method according to the invention.

DETAILED DESCRIPTION OF THE INVENTION

Figure 1:
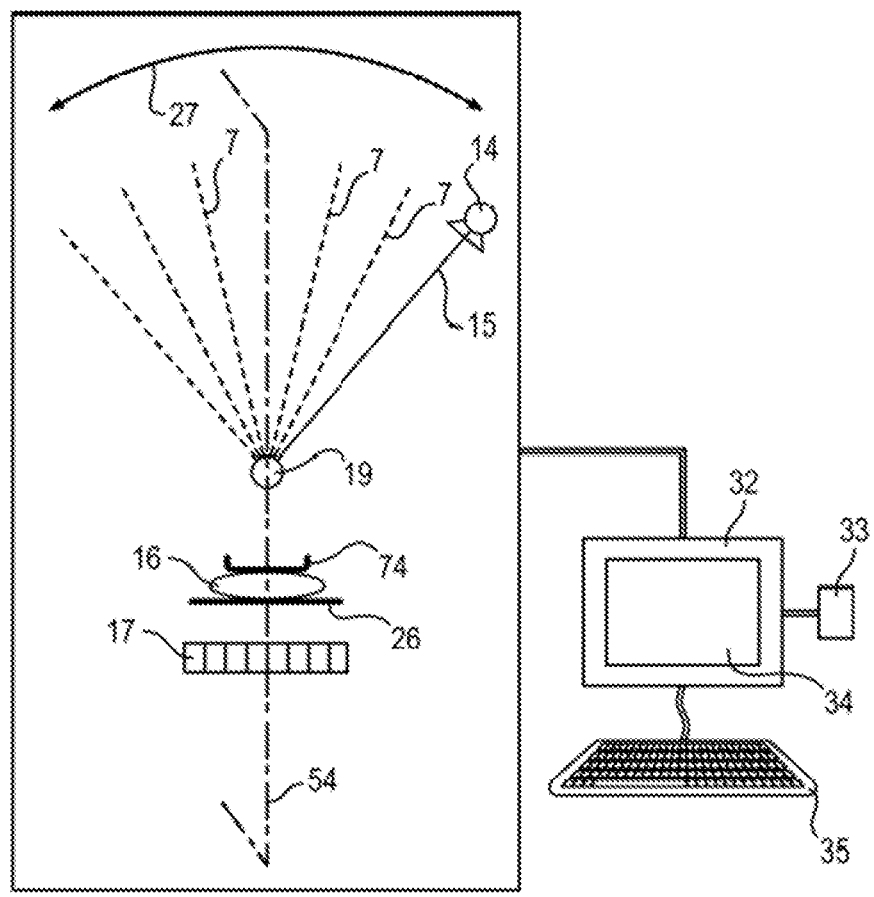
FIG. 1 is a schematic illustration of a tomosynthesis mammography system according to an embodiment of the invention.

FIG. 1 shows a medical imaging assembly 13. This assembly 13 comprises a radiation source 14, a mobile arm 15, an object support surface 26, a radiation detector 17, control means 31, processing means 32, and a paddle 74 positioned between the object support surface 26 and the source 14 for compression of an object to imaged 16.

The mobile arm 15 is able to be moved about a first axis 19 during a sequence of radiation exposures. The arm 15 acts as positioner. Each radiation exposure during the exposure sequence allows acquisition of a radiographic projection. After one exposure to radiation during the exposure sequence, the arm 15 is moved to permit acquisition of a radiographic projection of the object 16 to be imaged from a different angle.

In the embodiment of the medical imaging assembly 13 illustrated FIG. 3, the mobile arm 15 can be moved globally over a plane 60 (hereinafter designated as "plane of arm movement"). At one of its ends, the arm 15 carries the radiation source 14.

The radiation source 14 is capable of emitting radiation. The radiation source 14 is an X-ray source for example or any other type of radiation source known to the person skilled in the art.

During a sequence of exposures (for the acquisition of a plurality of radiographic projections from different angles) the irradiated field is maintained substantially constant by action on the collimation shutters of a collimator assembly (not shown) of the source. This action is synchronized with movement of the arm.

The radiation source 14 can be fixed to the mobile arm 15. In this case, on each movement of the mobile arm 15 from one position to another, the source 14 is moved in rotation about a first axis 19, so that the viewing directions of the source 14 meet at one same point inside the object 16, irrespective of the position of the arm 15. In this embodiment, the pathway of the source 14 is substantially an arc of a circle.

The radiation source 14 can be joined in translation with the mobile arm 15. In this case, on each movement of the arm 15, the source 14 is moved in rotation about the first axis 19 so that the viewing directions 21, 22, 23 meet at one same point 25 inside the object 16, and in translation along the arm 15, so that the pathway 27 of the source 14 during an exposure sequence is substantially rectilinear.

The object support surface 26 is able to receive the object 16 to be imaged. For example, in the case of mammography, the object 16 is the breast of a patient. However, the imaging assembly can be used to image other objects. The object support surface 26 illustrated FIG. 6 extends over one plane. The object support surface 26 is a plate for example.

The object support surface 26 is fixed for a sequence of exposures to radiation. However, the object support surface 26 can be moved manually or automatically between two sequences of exposure. For example, if the user has just completed reconstruction of three-dimensional data from a cranio-caudial view (CC) and wishes to obtain three-dimensional information from a mediolateral oblique view (MLO), the user can command pivoting of the object support surface 26 to place it in an oblique plane relative to a vertical plane, the object support surface and the other parts of the device (i.e. mobile arm, radiation source, radiation detector, etc.) being moved together to change over from CC to MLO.

The radiation detector 17 is capable of detecting the radiation emitted by the radiation source 14. The radiation detector 17 is for example a planar sensor or luminance amplifier associated with a camera.

The radiation detector 17 may comprise a matrix array consisting of an assembly of detection elements 29 distributed in rows and columns. The detection elements 29 detect the projected radiation which passes through the object 16. Each detection element 29 produces an electric signal which depends on the attenuation of the radiation emitted by the source 14. The radiation detector 17 may be substantially planar or curved.

The radiation detector 17 may be fixed during an exposure sequence to radiation. In this case, the radiation detector 17 is placed in a plane parallel to the plane of the object support surface 26 and at a distance from the object support surface 26 shorter than the distance between the source 14 and the object support surface 26 (typically 2 to 100 times shorter). However, similar to the object support surface 26, the radiation detector 17 can be moved in translation or moved in rotation between two exposure sequences to change over from CC acquisition mode for example to MLO acquisition mode. Also, the radiation detector 17 may be mobile during the sequence of exposures.

The radiation detector 17 may be mobile in translation. In this case, the radiation detector 17 is moved in translation along a direction parallel to the plane of the object support surface 26 and contained in the plane of movement 60 of the arm 15. In this embodiment, the pathway 28 of the detector 17 is substantially rectilinear.

The radiation detector 17 may be mobile in rotation about a rotation axis perpendicular to the plane of movement 60 of the arm 15 and passing through the intersection point of the viewing directions of the radiation source 14. In this embodiment, the pathway 28 of the detector 17 is substantially in an arc of a circle.

If the detector 17 is mobile during a sequence of exposures, the detector 17 is moved between two radiation exposures during the sequence of exposures.

The control means 31 are capable of controlling the radiation source 14, the radiation detector 17, the mobile arm 15 carrying the radiation source 14. The control means 31 are capable of controlling emission of radiation by the radiation source 14. The control means 31 are also capable of controlling the reading of an image by the radiation detector 17. In the embodiment comprising a mobile radiation detector 17, the control means 31 are capable of controlling movement of the detector 17 in translation and/or rotation.

In the embodiment, comprising the radiation source 14 joined in translation with the mobile arm 15, the control means 31 are capable of controlling translation of the source 14 along the mobile arm 15.

The control means 31 are also capable of controlling movement of the arm 15 about the first axis 19. During the sequence of radiation exposures, the control means 31 are capable of controlling movement of the arm 15 over a plurality of positions 51 lying between a first end position 52 and a second end position 53. The end positions 52, 53 correspond to the initial position and end position of the arm 15 during the sequence of radiation exposures.

The processing means 32 are capable of receiving the data provided by the radiation detector 17. The processing means 32 are capable of producing radiographic projections from data received from the radiation detector 17. The processing means 32 are also capable of implementing reconstruction methods allowing three-dimensional data to be obtained from radiographic projections. The display of a three-dimensional representation from three-dimensional data is preferably obtained per slice in planes parallel to the plane 55 of the object support surface 26.

The control means 31 and the processing means 32 are for example one or more computers, one or more processors, one or more microcontrollers, one or more micro-computers, one or more programmable logic controllers, one or more specific application integrated circuits, other programmable circuits or other devices which include a computer such as a work station.

In one embodiment, the control means 31 and the processing means 32 include a reading device (not shown) for example a disk reader or a CD-ROM reader to read the instructions of an instruction medium (not shown), such as a disk or a CD-ROM. In another embodiment, the processing means 32 carry out instructions stored in micro-software (not shown).

These instructions comprise instructions to implement a control method (such as described in the remainder hereof), and/or instructions to implement a method to reconstruct three-dimensional images from projected images (i.e. radiographic projections). The imaging assembly 13 also comprises memory means. The memory means are for example Read Only Memories (ROM) and Random Access Memories (RAM).

The memory means are coupled to the processing means 32 and can be integrated in or separated from the processing means 32. These memory means are used notably to store the radiographic projections and/or three-dimensional representations obtained at the output from the processing means 32.

The imaging assembly 13 also comprises an interface unit 35. The interface unit 35 comprises data entry means 35 and display means 34.

The data entry means enable the user to parameterize and control the acquisition of a sequence of radiation exposures. The data means comprise a mouse for example, a keyboard, or other peripherals which can be used for data entry by the user.

The display means allow display of the three-dimensional data obtained at the output of the processing means 32. The three-dimensional data can be displayed in slices of the imaged object 16, the slices extending over planes parallel to the plane 55 of the object support surface 26. The user can also control the interface to change over from one slice to another or to display several slices simultaneously by means of the data entry means. The display means are a conventional or specialized computer monitor, for example.

In one embodiment, the processing means 32 are coupled with an internal or external computer network 36. This allows remote users to control the processing means 32 (and the control means) remotely, for example to view results. The processing means 32 may also be coupled with other peripherals such as a printer 37 or additional, conventional or specialized computer monitors 38.

The operating principle of the system described above is the following. During a sequence of exposures to radiation, the arm 15 is moved over a plurality of positions to produce a set of radiographic projections acquired from different angles. For each position of the arm 15, the object 16 is exposed to radiation. More precisely the control means control movement of the C-arm over a plurality of positions 1, 2, 3.

For each position 1, 2, 3, the control means direct the radiation source to emit a radiation 10, 20, 30. This radiation illuminates the object to be imaged. Part of this radiation passes through the object and is detected by the radiation detector.

The radiation detector transmits the data recorded for each position of the source to the processing means. The processing means 32 produce a radiographic projection for each position of the source using the data received from the radiation detector 17. Each radiographic projection is therefore associated with a respective position of the radiation source.

On the basis of all the radiographic projections obtained for the different positions, the processing means 32 use reconstruction methods to obtain three-dimensional data.

To clarify the following description, the terms "point" and "zone" will be used to qualify the object, and the terms "voxel" and "region" will be used to qualify the three-dimensional representation. A point of the object is associated with a voxel of the three-dimensional representation. A zone of the object is associated with a region of the three-dimensional representation.

Figure 2:
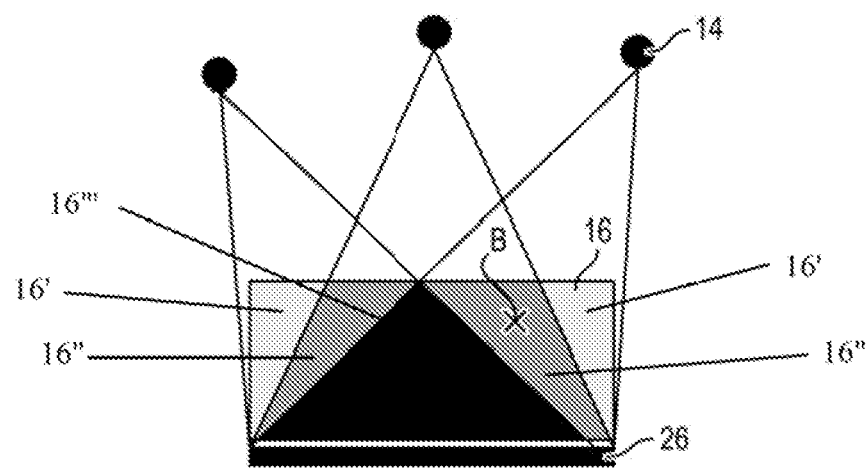
FIG. 2 is a schematic illustration of a tomosynthesis mammography system according to an embodiment of the invention.
Figure 3:
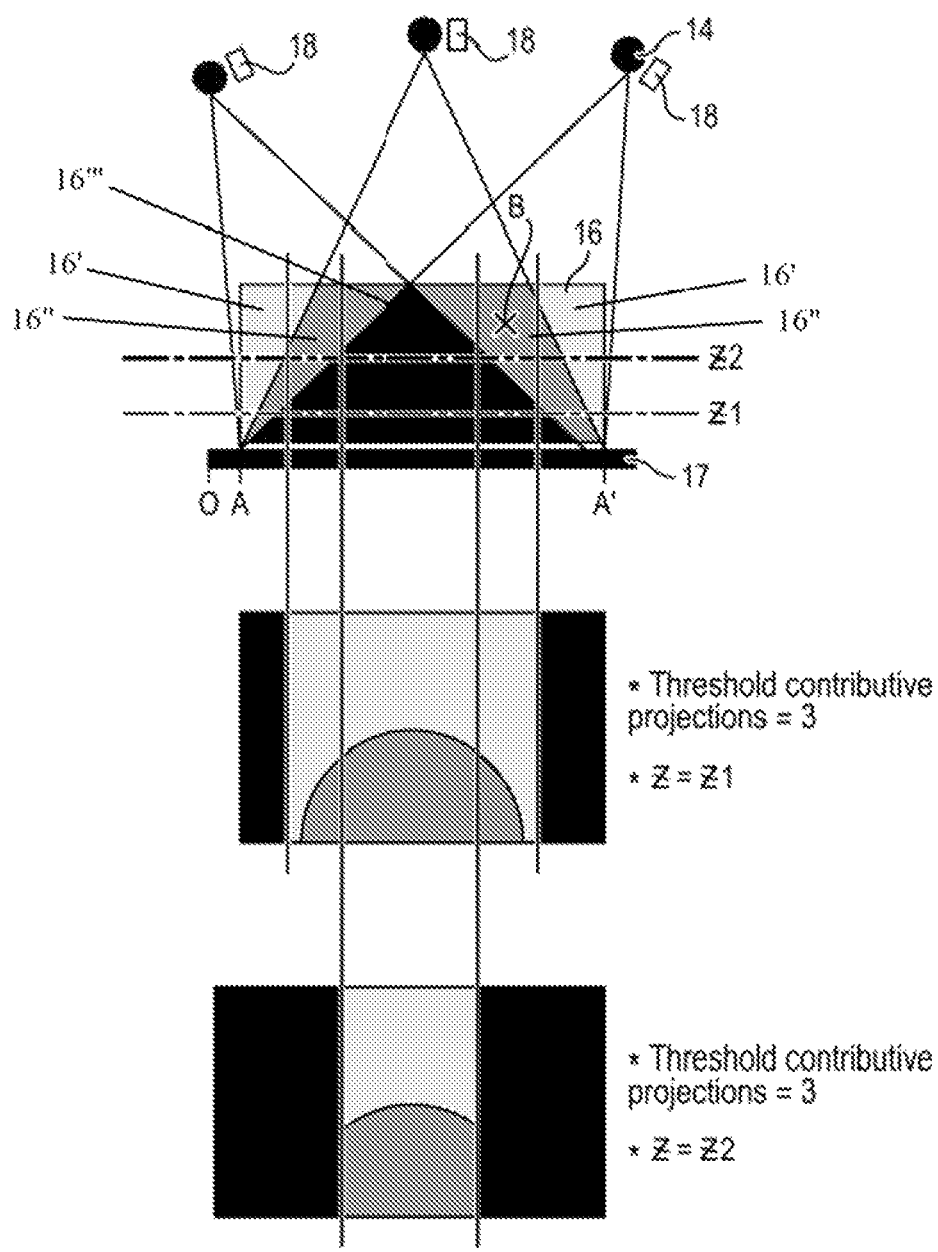
FIG. 3 is a schematic illustration of a tomosynthesis mammography system according to an embodiment of the invention.

With reference to FIGS. 2 and 3, an example of an acquisition sequence is illustrated in which three radiographic projections of an object 16 are acquired from different angles. The reader will appreciate that this example is simplified for better comprehension of the invention. Evidently, the reconstruction of a three-dimensional representation can be made using more than three radiographic projections. In particular in one variant of embodiment, the reconstruction of the three-dimensional representation of the object is made using nine radiographic projections.

On account of the shape of the object 16, the shape of the beam emitted by the source 14 and the angle position of the source 14 relative to the object 16, the radiation does not pass through some zones of the object 16 at certain positions of the source 14. Therefore, first zones 16' of the object 16 receive one ray, second zones 16" receive two rays, and third zones 16'" of the object receive three rays.

When reconstructing the three-dimensional representation of the object 16 from the radiographic projections: first regions—corresponding to the first zones 16' of the object—are reconstructed from a single radiographic projection, second regions—corresponding to the second zones 16" of the object—are reconstructed from two radiographic projections, and third regions—corresponding to the third zones 16'"—are reconstructed from three radiographic projections.

However, the quality of the information contained in the three-dimensional representation depends on the number of projections used to produce this data. The higher the number of radiographic projections used to reconstruct a voxel of the 3D representation, the better the quality of the reconstruction of said voxel.

It will therefore be appreciated that the quality of reconstruction of the different regions associated with the zones 16', 16'', 16''' of the object 16 varies in relation to the number of available projections—designated in the remainder hereof as "contributive projections"—to reconstruct these regions.

The invention proposes the use of means capable of determining the number of contributive projections for the reconstruction of each voxel of the three-dimensional representation.

In other words, the invention proposes the use of means capable of determining the number of projections in which at least one point of the object 16 located above or at the level of the object support surface 26 is present.

Notably, the invention proposes indicating to the user the number of contributive projections for each voxel of the reconstructed three-dimensional representation. This allows an indication to be given to the user on the quality of the information contained in the three-dimensional representation of each voxel. The indication on the number of contributive projections for each voxel can be of different types.

For this purpose, the processing means of the device are capable, for each point of a plane located above or at the level of the object support surface, of determining the effective number of projections contributing towards reconstruction of the three-dimensional data in the vicinity of this point, and thereby inferring the incidence on the quality of the reconstructed three-dimensional data. The device also comprises viewing means capable of presenting the user with information on the zone in which the quality of reconstructed three-dimensional data does not show any degradation resulting from use of an effective number of projections that is lower than a predetermined acceptable threshold.

In one embodiment, the viewing means comprise the display means. This allows the user, after acquisition and processing, to be presented with information on the zone in which the quality of the reconstructed three-dimensional data does not show any degradation resulting from use of an effective number of projections that is lower than a predetermined acceptable threshold.

The indication may be a colour code for example used on display of the three-dimensional representation. For example, the regions reconstructed from a single radiographic projection are displayed in yellow, the regions reconstructed from two radiographic projections are displayed in green, and the third regions reconstructed from three radiographic projections are displayed in blue.

The indication may also consist of markers or any other element known to the person skilled in the art. For example, in one embodiment, the contours of the different zones of the object are outlined using different types of line (dotted, solid, etc.)—or line thickness—in relation to the effective number of projections which allowed reconstruction of said zone.

In one embodiment, the presentation consists of displaying on the display means the number of projections used to reconstruct a voxel, for example when this voxel is selected by the user using a pointer displayed on the display means.

In another embodiment, the regions reconstructed from a number of radiographic projections higher than a threshold value entered by the user are displayed conventionally, the other regions (i.e. regions reconstructed from a number of radiographic projections lower than the threshold value) being shaded, not displayed or displayed in black. This makes it possible to focus the user's attention on the regions for which the quality of reconstruction is sufficient to allow determination of a diagnosis.

In one variant of embodiment, the processing means determine the number of contributive projections by calculating, for each voxel, the number of projections in which the corresponding point of the object 16 is present. One method to calculate the number of contributive projections for a voxel corresponding to a given point B of the object may for example be the following. A Euclidian frame of reference with origin o is defined, O being one of the ends of the object support surface for example.

As described previously, the irradiated field is maintained constant during an acquisition sequence. Therefore, in the Euclidian frame of reference of origin O, the coordinates (xA,yA,zA) and (xA',yA',zA') are known of the points A, A' of the object support surface 26 between which the radiations emitted by the source 14 are projected.

In this Euclidian frame of reference of origin O, the coordinates (xS, yS, zS) are also known from the source 14 for each position of the source 14 during the acquisition sequence.

It is therefore possible, in this Euclidian frame of reference of origin O, to define the equation of a cone—hereunder called "radiation cone"—representing the radiation emitted by the source 14 for a given position thereof. The equation of each radiation cone therefore corresponds to the radiation emitted by the source for each of its positions.

Knowing the equations of the different radiation cones, it is possible to determine whether point B of the object does or does not belong to the different cones.

Therefore, it is possible to determine the number of radiations passing through point B with coordinates (xB,yB,zB), and hence the number of contributive projections towards reconstruction of the voxel associated with point B of the object.

The reader will appreciate that, for a known acquisition sequence, the number of contributive projections for each voxel associated with a point located between the source 14 and the object support surface 26 may be previously calculated and stored in a database of numbers of contributive projections.

In this case, the processing means determine the number of projections contributing towards reconstruction of a voxel by looking for this number in this database.

In another embodiment, the viewing means comprise identification means. The identification means allow the locating of volume points lying between the source and the plane of the object support surface in which the reconstructed three-dimensional data does not show any degradation resulting from use of an effective number of projections that is lower than an acceptable threshold.

This makes it possible to provide the user, prior to acquisition and processing, with information on the zone in which the quality of reconstructed three-dimensional information does not show any degradation resulting from use of an effective number of projections that is lower than a predetermined acceptable threshold.

If the user wishes to observe a particular region whose quality of reconstruction is low, a new acquisition can be made by positioning the corresponding zone of the object on the object support surface 26 so that a sufficient number of rays pass through it.

For this purpose, the identification means may comprise illumination means 18. Preferably, these illumination means 18 are arranged in the vicinity of the radiation source 14.

In one variant of embodiment, the illumination means are capable of illuminating the volume points lying between the source and the plane of the object support surface in which the reconstructed three-dimensional data does not show any degradation resulting from use of an effective number of projections that is lower than an acceptable threshold. In another variant of embodiment, the illumination means 18 are capable of illuminating a portion of the object support surface 26 in which each illuminated point is present in a minimum number of contributive projections.

For example, the user enters a threshold value into the data entry means, corresponding to a minimum number of desired contributive projections.

The user can also enter the approximate height $z1$, $z2$—height with respect to the object support surface 26—of the point or zone it is desired to observe.

The illumination means then illuminate the object support surface 26 over a region whose illuminated points correspond to the points of the object 16 which will be present in a number of contributive projections that is equal to or more than the threshold value entered by the user (optionally in relation to the height entered by the user).

This enables the user to position the object 16 more easily on the object support surface 26 before the emission of radiation. Therefore, it is possible to limit the radiation dose emitted through the object 16.

The identification means may also comprise at least one video camera displaying an image of the object in which identification marks are superimposed designating the intersection of said volume with a plane of reference. This plane of reference may be the plane of the object support surface for example, or the plane of the paddle 74 placed between the object support surface 26 and the source 14 to compress the object 16 to be imaged.

The method of the invention will now be described in more detail with reference to FIG. 4. The medical imaging method of the invention comprises movement 100 of the source over a plurality of positions around the object support surface; for each position of the source, emission 200 by the radiation source to irradiate the object arranged on the object support surface; for each position of the source, detection 300 by the radiation detector of the radiation which has passed through the object; reconstruction 400 of the three-dimensional representation from all the acquired projections; determination 500, for each point of the object located above or at the level of the object support surface, of the number of projections in which said point is present; and display 600 of the three-dimensional representation.

The determination step 500 can determine the number of contributive projections contributing towards reconstruction of each voxel of the three-dimensional representation.

This number of contributive projections for each voxel can then be displayed on the display means as described previously, or can be indicated by a marker or colour code.

The system and method of the invention can notably provide the user with a set of performance indicators enabling the user to better apprehend the quality of the three-dimensional data presented. This facilitates determination of diagnosis by the user. By determining the number of contributive projections for the reconstruction of each voxel, with the system and method of the invention, the user is able to quantify the relative importance of the different voxels.

Although the medical imaging assembly and associated method described above have been presented with respect to an arm able to be moved over a plane, the movement of the arm may be more complex. For example, in another embodiment, the carrier arm is able to be moved about several axes of rotation.

What is claimed is:

1. A medical imaging device, comprising:
   an object support surface;
   a radiation source to emit radiation, said source movable in a plurality of positions around the object support surface;
   a radiation detector configured to detect the radiation emitted by the source, the radiation source emitting radiation which is received by the detector at each position, so as to obtain a plurality of projections corresponding to the plurality of positions of the radiation source;
   a processor which, for each point in a plane located above or at a level of the object support surface, is configured to determine an effective number of projections contributing towards reconstruction of the three-dimensional data in the vicinity of a predetermined point, and to infer from this determination an incidence on the quality of the reconstructed three-dimensional data; and
   a viewing device configured to present information on a zone in which the quality of reconstructed three-dimensional data does not show any degradation resulting from use of an effective number of projections that is lower than a predetermined threshold, wherein the viewing device comprises an identification device which, prior to acquiring the plurality of projections, is configured to locate volume points lying between the source and the plane of the object support surface in which the reconstructed three-dimensional data does not show any degradation resulting from use of an effective number of projections that is lower than the threshold, wherein the identification device comprises an illumination device to illuminate said volume points.

2. The medical device of claim 1, wherein the viewing device comprises:
   a display device configured to display a three-dimensional representation reconstructed from the plurality of projections,
   wherein said display device is also configured to present information on the zone in which the quality of the reconstructed three-dimensional representation does not show any degradation resulting from the use of an effective number of projections that is lower than the predetermined threshold.

3. The medical device of claim 2, wherein the display device is configured to superimpose a different marker for each region of the three-dimensional representation in relation to the effective number of projections used to reconstruct said region.

4. The medical device of claim 2, wherein the display device is configured to mask a zone whose quality does show degradation resulting from use of an effective number of projections that is lower than the predetermined threshold.

5. The medical device of claim 2, wherein the display device is configured to display differently:
   a zone reconstructed from an effective number of projections higher than the predetermined threshold; and
   the zone reconstructed from an effective number of projections that is lower than the predetermined threshold.

6. The medical device of claim 1, wherein the identification device comprises an illumination device to illuminate the surfaces of the object support surface limiting said volume points.

7. The medical device of claim 1, wherein the identification device comprises at least a video camera configured to display an image of an object on which marks are superimposed designating the intersection of said volume points with a reference plane.

8. The medical device of claim 1, wherein the illumination device is configured to illuminate the object support surface over a region whose illuminated points correspond to the points of an object which will be present in a number of contributive projections that is equal to or more than the threshold value.

9. A medical imaging method, comprising:
moving a radiation source over a plurality of positions about an object support surface;
emitting the radiation source at each position, to irradiate an object arranged on the object support surface;
detecting, for each position of the source, by a radiation detector of the radiation which has passed through the object, so as to obtain a plurality of radiographic projections;
reconstructing a three-dimensional representation from the radiographic projections;
determining, for each point in a plane located above or at the level of the object support surface, of the number of projections contributing towards reconstruction of the three-dimensional data in the vicinity of this point, and inferring the incidence on the quality of the reconstructed three-dimensional data; and
identifying, prior to emitting the radiation source, volume points lying between the source and the plane of the object support surface in which the reconstructed three-dimensional data does not show any degradation resulting from use of an effective number of projections that is lower than the threshold and illuminating said volume points;
presenting information on a zone in which the quality of reconstructed three-dimensional data does not show any degradation resulting from use of an effective number of projections that is lower than a predetermined threshold.

10. A medical imaging device, comprising:
an object support surface;
a radiation source to emit radiation, the source movable in a plurality of positions around the object support surface;
a radiation detector configured to detect the radiation emitted by the source, the radiation source emitting radiation which is received by the detector at each position, so as to obtain a plurality of projections corresponding to the plurality of positions of the radiation source;
a processor which, for each point in a plane located above or at a level of the object support surface, is configured to determine an effective number of projections contributing towards reconstruction of the three-dimensional data in the vicinity of a predetermined point, and to infer from this determination an incidence on the quality of the reconstructed three-dimensional data; and
a viewing device configured to present information on the quality of reconstructed three-dimensional data of at least one zone within the reconstructed three-dimensional data based on the effective number of projections contributing to each of the at least one zone, wherein the viewing device comprises an identification device which, prior to acquiring the plurality of projections, is configured to locate volume points lying between the source and the plane of the object support surface in which the reconstructed three-dimensional data does not show any degradation resulting from use of an effective number of projections that is lower than the threshold, wherein the identification device comprises an illumination device to illuminate said volume points.

* * * * *